United States Patent [19]

Pugach et al.

[11] Patent Number: 5,072,051
[45] Date of Patent: * Dec. 10, 1991

[54] PREPARATIION OF METHYL ISOPROPENYL KETONE

[75] Inventors: Joseph Pugach, Monroeville Boro; Jeffrey S. Salek, Oakdale Boro, both of Pa.

[73] Assignee: Aristech Chemical Corporation, Pittsburgh, Pa.

[*] Notice: The portion of the term of this patent subsequent to Jul. 3, 2007 has been disclaimed.

[21] Appl. No.: 559,804

[22] Filed: Jul. 30, 1990

Related U.S. Application Data

[63] Continuation-in-part of Ser. No. 367,902, Jun. 19, 1989, Pat. No. 4,945,184, and a continuation-in-part of Ser. No. 508,454, Apr. 13, 1990, Pat. No. 5,004,839, which is a continuation-in-part of Ser. No. 425,269, Oct. 23, 1989, abandoned.

[51] Int. Cl.$^5$ .............................................. C07C 45/75
[52] U.S. Cl. ................................................... 568/390
[58] Field of Search ........................ 568/313, 345, 340

[56] References Cited

U.S. PATENT DOCUMENTS

| | | | |
|---|---|---|---|
| 2,064,564 | 12/1936 | Quattlebaum, Jr. ................. | 260/134 |
| 2,245,567 | 6/1941 | Brant et al. ......................... | 260/593 |
| 2,451,351 | 10/1948 | Mottern et al. ..................... | 260/593 |
| 2,462,031 | 2/1949 | Wittcoff .............................. | 260/333 |
| 2,549,508 | 4/1951 | Mottern ............................... | 260/586 |
| 3,077,500 | 2/1963 | Heinz et al. ......................... | 260/594 |
| 3,422,148 | 1/1969 | Wollner et al. ..................... | 260/593 |
| 4,005,147 | 1/1977 | Fischer et al. ................... | 260/593 R |
| 4,035,395 | 7/1977 | Stetter et al. ..................... | 260/347.5 |
| 4,374,274 | 2/1983 | Heilen et al. ........................ | 568/313 |

OTHER PUBLICATIONS

Mironov et al., "Synthesis of alpha, beta-unsaturated Ketones", Yaroslavl' Technological Institute, translated from Zhurnal Prikadnoi Khimii, vol. 36, No. 3, pp. 654–662, Mar. 1963.

Primary Examiner—James H. Reamer
Attorney, Agent, or Firm—William L. Krayer

[57] ABSTRACT

Methyl isopropenyl ketone is produced from methyl ethyl ketone and paraformaldehyde under mild reaction conditions utilizing a catalyst comprising a halogen acid salt of a secondary amine and (a) a non-soluble solid oxide of an element selected from Groups IB, IIIA, IVA, IVB, VA, VB, VIB and VIII of the periodic table, or (b) a carboxylic acid. Temperatures of 120–150 and pressures of 700–1400 kpa are preferred; co-products may include ethyl vinyl ketone.

23 Claims, No Drawings

// PREPARATION OF METHYL ISOPROPENYL KETONE

RELATED APPLICATIONS

This is a continuation-in-part of two prior applications of two of the inventors herein (J. Pugach and J. Salek), namely of application Ser. No. 367,902, filed June 19, 1989, now U.S. Pat. No. 4,945,184 entitled "Preparation of Unsaturated Ketones" and application Ser. No. 508,454, filed Apr. 13, 1990, now U.S. Pat. No. 5,004,839 entitled "Preparation of Unsaturated Ketones from Acetone and Paraformaldehyde (II)", the entire specifications and claims of which are incorporated herein by reference. Application Ser. No. 508,454 is in turn a continuation-in-part-of application Ser. No. 425,269, filed Oct. 23, 1989, now abandoned entitled "Preparation of Vinyl Ketones from Acetone and Paraformaldehyde (II)".

TECHNICAL FIELD

This invention relates to the conversion of methyl ethyl ketone to methyl isopropenyl ketone. Typical is the reaction of methyl ethyl ketone with paraformaldehyde at temperatures of about 120°-150° C. and pressures of 700-1400 kilopascals in the presence of a solid catalyst comprising one or more oxides of elements of Groups IB, IIIA, IVA, IVB, VA, VB, VIB and VIII of the periodic table and a halogen acid salt of a secondary amine. We may also use a catalyst comprising a halogen acid salt of a secondary amine and a small amount of a carboxylic acid. Methyl isopropenyl ketone (MIPK) is of current interest as a comonomer for photodegradable plastics and as a photosensitizer, and may be used as a comonomer in various other plastics and resins.

BACKGROUND OF THE INVENTION

Prior to the present invention, it has been known to react formaldehyde with acetone to obtain methyl vinyl ketone and with various other See Ember U.S. Pat. No. 3,928,457.

A general reaction for the preparation of an alpha, beta unsaturated ketone by catalytic vapor phase condensation of formaldehyde and a ketone is disclosed in U.S. Pat. No. 3,928,458.

In Mottern U.S. Pat. No. 2,549,508, Example V, methyl ethyl ketone is reacted in the vapor phase with formaldehyde in the presence of a solid mixture of zinc oxide and zirconium oxide to form methyl isopropenyl ketone.

The literature also teaches the separate use of secondary amines and strong acid or weak acid salts of secondary amines for the reaction of ketones and, primarily, aldehydes, with aqueous formaldehyde (monomeric) to form the corresponding vinyl aldehyde and ketones (see Ai, M. J., *Catal.*, 1987, 106, 2734; Ueda, W. Yokoyama, T., Moro-Oka, Y., Ikawa, T., *J. Chem. Soc., Chem. Commun.*, 1984, 39 ; Gutsche, D. C., Nam., K.C., *J. Am. Chem. Soc.*, 1988, 110, 6153; U.S. Pat. Nos. 4,275,242, 4,343,239, 4,406,079 and 4,496,770). A tertiary amine is used in U.S. Pat. No. 3,077,500.

The reader may also be interested in reviewing U.S. Pat. Nos. 3,928,450 and 3,701,798. The '798 patent uses an oxide of a rare earth metal as a catalyst.

In Heinz et al U.S. Pat. No. 3,077,500, methyl ethyl ketone is reacted with aqueous formaldehyde in the presence of a tertiary amine with and without anion exchange resin catalysts. However, methyl isopropenyl ketone is obtained only by dehydrogenating the reaction product.

U.S. Pat. No. 3,422,148 also discloses a method of making methyl isopropenyl ketone. In this process, methyl ethyl ketone is reacted with aqueous formaldehyde in the presence of an "acidic cation exchange resin." No paraformaldehyde is mentioned; applicants' catalyst is different.

The use of paraformaldehyde in the manufacture of certain saturated carbonyl-containing compounds is suggested in U.S. Pat. No. 4,374,274. The process further differs from that disclosed herein in that it employs a palladium catalyst deposited on a particular phosphate base.

SUMMARY OF THE INVENTION

Our invention is a method of making methyl isopropenyl ketone comprising reacting para-formaldehyde with methyl ethyl ketone in the presence of an amine catalyst of the formula $R^1R^2NH$, a halogen acid (the amine may be in the form of a halogen acid salt), preferably in an amount about equimolar to the amine, and either (1) a solid catalyst selected from the group consisting of non-soluble oxides of elements (as further explained below) of Groups IB, IIIA, IVA, IVB, VA, VB, VIB and VIII of the periodic table, specifically the periodic table as published in the 61st edition of Chemical Rubber Company's Handbook of Chemistry and Physics or (2) a carboxylic acid as explained below. The ratio of methyl ethyl ketone to formaldehyde (which is in the form of paraformaldehyde) is not critical, but is advantageously a molar ratio of about 10:1 to about 1:10, preferably about 5:1 to about 1:1. In the higher ratios within this range, formaldehyde conversions of 95-100% are obtained with an equimolar amount of methyl ethyl ketone being consumed, while the selectivity to methyl isopropenyl ketone is 50-60% with ethyl vinyl ketone typically co-produced at about 20-30%. Ketone conversions approaching 100% based on paraformaldehyde consumption are common in the higher ratios within these ranges. Temperatures may range from about 50° C. to about 250° C., preferably 120°-150° C., and pressures from atmospheric to about 1600, preferably 700-1400 kilopascals. Use of an inert atmosphere such as argon or nitrogen is preferred but not essential. Inert solvents may be used if desired to dilute the reactants but are not necessary. In batch processing, the reaction should be conducted for at least 0.25 hours, with 1-2 hours being preferred, depending on the other conditions. Reaction times beyond ten hours confer no further advantage. A stabilizer such as hydroquinone may also be used as known in the art to prevent polymerization of the unsaturated product.

As mentioned above, our invention also includes the reaction of methyl ethyl ketone with paraformaldehyde in the presence of an amine catalyst of the formula $R^1R^2NH$, a halogen acid (which may form a salt with the amine), preferably in an amount about equimolar to the amine, and a small amount of an aliphatic or an aromatic carboxylic acid having up to about 15 carbon atoms. $R^1$ and $R^2$ may be independently selected alkyl or aryl groups having up to about 20 carbon atoms. The ratio of methyl ethyl ketone to formaldehyde (which must be in the form of paraformaldehyde) is not critical, but is advantageously about 10:1 to about 1:10; preferably about 5:1 to about 1:1. In the higher ratios within this range, formaldehyde conversions of 95-100% are obtained with an equimolar amount of ketone feed being consumed, while selectivities to vinyl ketones are 70–100%. At lower ratios, ketone conversions of 30–50% are observed with selectivities to vinyl ketones based on the starting ketone of 70–85%. Temperatures may range from about 50° C. to about 250° C., preferably 120°–150° C., and pressures from atmospheric to about 1500, preferably 700–1400 kilopascals. Use of an inert atmosphere such as argon or nitrogen is preferred but not essential. Inert solvents such as acetonitrile or 1,4-dioxane may be used if desired to dilute the reactants, but are not necessary. In batch processing, the reaction should be conducted for at least 0.25 hours, with 1–2 hours being preferred, depending on the other conditions. Reaction times beyond ten hours confer very little further advantage. A stabilizer such as hydroquinone may also be used as known in the art to prevent polymerization of the unsaturated product.

Our invention has the advantage that the presence of water is minimized, in addition to obtaining excellent yields and selectivities under relatively mild conditions, employing in the preferred mode a metal oxide or similar co-catalyst which may be recycled or reused relatively easily. It was surprising and unexpected how well paraformaldehyde worked (in the presence of our catalysts) since it is assumed in the literature that paraformaldehyde decomposes to the monomer (the normally reactive species) only in the presence of strong acids (see Bevington, T., Q. Rev., Chem. Soc., 1952, 6, 141.; U.S. Pat. Nos. 4,340,767; 3,925,488 and 3,026,264; Japan Patent 59 55,849; Process Economics Program (Formaldehyde; Report No. 23), Stanford Research Institute, Menlo Park, California, 1967, pp. 45–46, 154. Trioxane is also ineffective. While the reaction itself generates water, our process minimizes the amount of water present. We have found in our invention that paraformaldehyde provides much higher conversions and selectivities than aqueous formaldehyde. Moreover, and perhaps most important, our process produces no detectable ketone condensation products.

Examples of suitable nonsoluble oxides for use in our catalyst are niobium oxide, tungsten oxide, hafnium oxide, iron oxide, nickel oxide, titanium oxide, vanadium oxide, and aluminum oxide. The oxide is used together with a halogen acid salt of a secondary amine of the formula $R^1R^2NH$ where $R^1$ and $R^2$ have the meanings stated above, in a weight ratio of amine (exclusive of the associated acid) to oxide of from about 0.5:1 to about 10:1. The reaction is preferably conducted in the presence of an inert gas.

By non-soluble, we mean not soluble under the conditions of the reaction in either an organic or inorganic medium which is present. It will be seen in the examples below that the oxides also include the insoluble acids of the oxides which can be formally thought of as the hydration products of the oxides. Examples of these acids are: niobic acid, tungstic acid, silicic acid and the like. Accordingly, we use the phrase "non-soluble oxide of an element" of the designated periodic table groups to describe the materials we employ; fragments such as $WO_4$ must be present as non-soluble compounds. Certain insoluble phosphates are operable in our invention; however, we do not employ phosphoric acid or any of the readily soluble phosphates such as trisodium phosphate or any other soluble alkali metal compounds. Thus, the oxygen-containing compounds we employ are the nonsoluble oxides of elements of Groups IB, IIIA, IVA, IVB, VA, VB, VIB and VIII of the periodic table.

When we speak of the medium which is present and in which the solid catalyst is not soluble, we refer typically to the liquid reactants such as the ketone feed, water produced as a by-product. and the desired ketone products. Other potential solvent media are aliphatic hydrocarbons, aromatic hydrocarbons, ethers, and nitriles. However, solvents are not necessary. We intend for our solid catalysts to be soluble in none of these under the conditions of the reaction. The potential solvents in the reaction mixture may be generally defined as those which are non-reactive under the reaction conditions.

The solid catalyst may be utilized in a bed or in a slurry; the reaction may be conducted continuously or batch-wise. A preferred solid catalyst is niobium oxide.

The amine catalyst may comprise a reaction product, i.e. a combination of a secondary amine and an acid salt such as hydrochloric acid. Examples of suitable amines are piperidine, dibutyl amine, diphenylamine, piperazine, dioctyl amine, diethyl amine, dipropyl amine, pentyl n-butyl amine, diisobutylamine, dihexyl amine and the halogen acid salts thereof.

The amine catalyst should be present in an amount representing from about 0.01 to about 0.1 equivalent per equivalent of the starting methyl ethyl ketone feed.

In the Examples below, the results are shown for various experiments including some conducted according to the general (basic) procedure which follows, typified experiments "c" or "j".

To a pressure vessel (Parr autoclave) methyl ethyl ketone (1 equiv.), paraformaldehyde (0.25 equiv.), a secondary amine hydrohalogen salt (0.025 equiv.), a solid acid catalyst, or a carboxylic acid as described below, (0.010 equiv.) and hydroquinone (0.001 equiv.) were added. With mechanical stirring, the reaction was run for one hour at 135° C. under initially from about 400–800 kilopascals, then increased to the range 700–1400 kpa. Results are shown in the Table below; MEK conversions are expressed based on reacted formaldehyde. Variations from the basic procedure are set forth in the footnotes following the Table.

TABLE I

| Expt. | MEK conv'n. | MIPK /EVK | MIPK SEL | EVK SEL | IVK SEL |
|---|---|---|---|---|---|
| a | 21% | 12/88 | 6% | 46% | 1% |
| b | 36% | 12/88 | 2% | 15% | 0.25% |
| c | 100% | 70/30 | 57% | 26% | 4% |
| d | 87% | 66/34 | 54% | 28% | 4% |
| e | 100% | 76/24 | 63% | 20% | 3% |
| f | 100% | 69/31 | 57% | 26% | 5% |
| g | 30% | 65/35 | 42% | 23% | 4% |
| h | 70% | 69/31 | 42% | 19% | 3% |
| i | 94% | 66/34 | 57% | 30% | 5% |
| j | 100% | 69/31 | 56% | 25% | 4% |
| k | 100% | 75/25 | 56% | 18% | 4% |
| l | 100% | 76/24 | 53% | 17% | 3% |
| m | 100% | 76/24 | 54% | 17% | 4% |
| n | 100% | 99/1 | 37% | 0.25% | <1% |
| o | 100% | 76/24 | 70% | 22% | 2% |
| p | 80% | 71/29 | 56% | 23% | 4% |
| q | 38% | 71/29 | 39% | 16% | 4% |
| r | 34% | 72/28 | 40% | 16% | 3% |
| s | 100% | 70/30 | 53% | 23% | 3% |
| t | 60% | 65/35 | 48% | 26% | <1% |
| u | 71% | 65/35 | 50% | 27% | 4% |
| v | 100% | 65/35 | 48% | 26% | 4% |
| w | 100% | 67/33 | 50% | 24% | 5% |
| x | 100% | 68/32 | 51% | 24% | 6% |
| y | 100% | 69/31 | 51% | 23% | 6% |
| z | 57% | 59/41 | 32% | 22% | 1% |

TABLE I-continued

| Expt. | MEK conv'n. | MIPK /EVK | MIPK SEL | EVK SEL | IVK SEL |
| --- | --- | --- | --- | --- | --- |
| aa | 51% | 56/44 | 31% | 24% | <1% |

The experiments a-aa included the following variations:
a. Dibutylamine used without a solid catalyst.
b. Dioctylamine used without a solid catalyst.
c. Piperidine hydrochloride and niobium oxide.
d. "c" repeated with no niobium oxide.
e. Dimethylamine hydrochloride used rather than piperidine hydrochloride as in "c".
f. Diethylamine hydrochloride used rather than piperidine hydrochloride as in "c".
g. Orthophosphoric acid salt of diethylamine used rather than piperidine hydrochloride as in "c".
h. Hydrobromic acid salt of diethylamine used rather than piperidine hydrochloride as in "c".
i. Ethylmethylamine hydrochloride used rather than piperidine hydrochloride as in "c".
j. "c" repeated using propionic acid rather than niobium oxide.
k. "c" repeated using acetic acid rather than niobium oxide.
l. "c" repeated using butyric acid rather than niobium oxide.
m. "c" repeated using isobutyric acid rather than niobium oxide.
n. P-toluene sulfonic acid used rather than any other catalyst.
o. 8:1 MEK:paraformaldehyde; otherwise as in "c".
p. 3:1 MEK:paraformaldehyde; btherwise as in "c".
q. 1:1 MEK:paraformaldehyde using niobium oxide/-piperidine hydrochloride.
r. 1:1 MEK:paraformaldehyde using niobium oxide/-piperidine hydrochloride.
s. "c" repeated using recycled niobium oxide.
t. "g" repeated except that 16% by weight water added.
u. "c" repeated at 125° C. rather than 135° C.
v. "c" repeated except that zirconium oxide used rather than niobium oxide.
w. "c" repeated except that tungstic acid used instead of niobium oxide.
x. "c" repeated except that hafnium oxide used instead of niobium oxide.
y. "c" repeated except that titanium oxide used instead of niobium oxide.
z. aqueous methanolic formaldehyde instead of paraformaldehyde (4:1 MEK:formaldehyde) using niobium oxide/diethylamine hydrochloride.
aa. Same as "z" except uninhibited aqueous formaldehyde.

GC analysis commonly revealed MEK (methyl ethyl ketone) conversions of 90-100% based on reacted formaldehyde and methyl isopropenyl ketone (MIPK) and ethyl vinyl ketone (EVK) selectivities of 50-60% and 20-30%, respectively. The balance of the product was isopropenyl vinyl ketone (IVK).

The niobium oxide ($Nb_2O_5$) catalyst was prepared as follows:

To a 2-liter three-necked round bottom flask equipped with a mechanical stirrer, a thermometer and a dropping funnel, was added 500ml of deionized water. Then 100g of $NbCl_5$ (obtained from Cerac, Inc.) was slowly added to the water with good agitation, and at such a rate that the temperature of the mixture did not go above 50° C. After addition was complete, stirring was continued for an additional 0.5 hours at which point 257ml of 28% aqueous ammonia was added in the period of 0.5 hours. Stirring of the slurry was continued for an additional 0.5 hours, and the slurry was then filtered through a coarse fritted vacuum funnel. The cake so collected was then put back into the flask and washed with 500 ml of fresh deionized water with good stirring for 15 minutes and the filtration and washing procedure was repeated until the pH of the final wash solution was 6.5-7.0. The hydrated niobium oxide was then dried to a constant weight in a drying oven at 150° C. Treatments at higher temperatures were done for three hours in a muffle furnace.

It should be noted that when using our process which does not employ a solid oxide catalyst, the process is sensitive to the presence of the carboxylic acid—that is, when we ran the reaction of methyl ethyl ketone and paraformaldehyde (polymer) in the presence of secondary amines or their salts (with no carboxylic acid present, and, no solid catalyst), poorer results were obtained. While a very small amount of carboxylic acid will have at least some beneficial effect in this process, we have found that about 0.01 equivalent of carboxylic acid per equivalent of methyl ethyl ketone is an optimum; use of greater amounts will not produce commensurately more beneficial results. At least about 0.005 equivalent RCOOH is preferred. Furthermore, it was surprising and unexpected how well paraformaldehyde worked (only in the presence of our catalyst) since it is known that paraformaldehyde decomposes to the monomer (the normally reactive species) only in the presence of strong acids and at temperatures approximating 170° C. (see Bevington, T., Q. Rev., Chem. Soc., 1952, 6, 141.; U.S. Pat. Nos. 4,340,767; 3,925,488 and 3,026,264; Japan Patent 59 55,849; Process Economics Program (Formaldehyde; Report No. 23), Stanford Research Institute, Menlo Park, California, 1967, pp. 45-46, 154. 1, 3, 5-Trioxane (the cyclic trimer of formaldehyde) also gave poor results with our catalyst system, again demonstrating the uniqueness of the paraformaldehyde/-catalyst combination.

The catalyst may comprise a reaction product, i.e. a combination of a secondary amine and an acid salt such as hydrochloric acid. Examples of suitable amines are piperidine, dibutyl amine, piperazine, dioctyl amine, diethyl amine, dipropyl amine, pentyl n-butyl amine, diisobutylamine, dihexyl amine and the halogen acid salts thereof. Examples of suitable carboxylic acids are those having up to about 18 carbon atoms such as acetic, propionic, succinic, benzoic, malic, stearic acid and the like. We prefer carboxylic acids having about 2 to 5 carbon atoms. The molar ratio of amine acid salt to the carboxylic acid may be about 0.5:1 to about 10:1, preferably about 2.5:1.

The amine catalyst should be present in an amount representing from about 0.01 to about 0.1 equivalent per equivalent of the starting ketone feed.

We claim:

1. Method of making methyl isopropenyl ketone comprising reacting methyl ethyl ketone and paraformaldehyde in the presence of a secondary amine hydrohalide and a catalyst selected from (a) a carboxylic acid having up to about 15 carbon atoms and (b) a solid non-soluble oxide of an element of Group IB, IIIA, IVA, VA, VB, VIB and VIII of the periodic table.

2. Method of making methyl isopropenyl ketone comprising reacting methyl ethyl ketone with paraformaldehyde in the presence of an amine catalyst of the formula $R^1R^2NH$, a halogen acid, and a solid catalyst selected from the group consisting of non-soluble oxides of elements of Groups IB, IIIA, IVA, IVB, VA, VB, VIB and VIII of the periodic table, where $R^1$ and $R^2$ are independently selected alkyl or aryl groups having up to about 20 carbon atoms or forming hetero groups in combination having up to about 20 carbon atoms.

3. Method of claim 2 wherein the ratio of methyl ethyl ketone to paraformaldehyde is about 10:1 to about 1:10.

4. Method of claim 2 wherein the ratio of methyl ethyl ketone to paraformaldehyde is about 5:1 to about 1:1.

5. Method of claim 2 wherein the temperature is maintained in the range of about 50° C. to about 250° C.

6. Method of claim 2 wherein the pressure is maintained at about 700-1400 kilopascals.

7. Method of claim 2 wherein the amine catalyst is present in an amount from about 0.01 equivalent to about 0.1 equivalent with respect to the methyl ethyl ketone reactant.

8. Method of claim 2 wherein the halogen acid is present in the form of a salt of the amine catalyst.

9. Method of claim 2 wherein the solid catalyst is present in an amount from about 0.0025 to about 0.1 equivalent with respect to the methyl ethyl ketone reactant.

10. Method of claim 2 wherein the solid catalyst is present in an amount from about 0.01 to about 0.025 equivalent with respect to the methyl ethyl ketone reactant.

11. Method of claim 2 wherein the solid catalyst is niobium oxide.

12. Method of making methyl isopropenyl ketone and ethyl vinyl ketone comprising reacting paraformaldehyde with methyl ethyl ketone in the presence of a catalyst which is a halogen acid salt of an amine of the formula $R^1R^2NH$, where $R^1$ and $R^2$ are independently selected alkyl or aryl groups having up to about 20 carbon atoms or forming hetero groups in combination having up to about 20 carbon atoms, and a solid catalyst selected from the group consisting of non-soluble oxides of elements of Groups IB, IIIA, IVA, IVB, VA, VB, VIB and VIII of the periodic table.

13. Method of claim 12 wherein the solid catalyst is present in a bed.

14. Method of claim 12 wherein the solid catalyst is niobium oxide.

15. Method of making a methyl isopropenyl ketone and ethyl vinyl ketone comprising reacting methyl ethyl ketone with paraformaldehyde in the presence of an amine catalyst of the formula $R^1R^2NH$, a halogen acid, and a small amount of a carboxylic acid having up to about 15 carbon atoms, where $R^1$ and $R^2$ are independently selected alkyl or aryl groups having up to about 20 carbon atoms.

16. Method of claim 15 wherein the ratio of methyl ethyl ketone to paraformaldehyde is about 10:1 about 1:10.

17. Method of claim 15 wherein the ratio of methyl ethyl ketone to paraformaldehyde is about 5:1 to about 1:1.

18. Method of claim 15 wherein the temperature is maintained in the range of about 50° C. to about 250°.

19. Method of claim 15 wherein the pressure is maintained at about 700-1400 kilopascals.

20. Method of claim 15 wherein the amine catalyst is present in an amount from about 0.01 to about 0.1 equivalent with respect to the methyl ethyl ketone reactant.

21. Method claim 15 wherein the halogen acid is present in the form of a salt of the amine catalyst.

22. Method of claim 15 wherein the ratio of amine acid salt to carboxylic acid is about 0.5:1 to about 10:1.

23. Method of claim 15 wherein the carboxylic acid is propionic acid.

* * * * *

UNITED STATES PATENT AND TRADEMARK OFFICE
CERTIFICATE OF CORRECTION

PATENT NO.   : 5,072,051
DATED        : December 10, 1991
INVENTOR(S)  : Joseph Pugach, et. al.

It is certified that error appears in the above-identified patent and that said Letters Patent is hereby corrected as shown below:

Column 1, line 40, after "other" insert -- ketones to obtain corresponding unsaturated ketones--.

Column 5, line 34, "btherwise" should be -- otherwise --.

Signed and Sealed this

Twenty-third Day of March, 1993

*Attest:*

STEPHEN G. KUNIN

*Attesting Officer*   Acting Commissioner of Patents and Trademarks